United States Patent [19]

Shrotryia et al.

[11] Patent Number: 4,777,173

[45] Date of Patent: Oct. 11, 1988

[54] METHOD FOR TREATMENT OF ALCOHOL ABUSE

[75] Inventors: Rajesh Shrotryia, Woodbridge, Conn.; George P. Casten, Evansville, Ind.

[73] Assignee: Bristol-Myers Company, New York, N.Y.

[21] Appl. No.: 30,659

[22] Filed: Mar. 25, 1987

[51] Int. Cl.$^4$ .................. A61K 31/50; A61K 31/495
[52] U.S. Cl. ...................................... 514/252; 514/811
[58] Field of Search ............................... 514/252, 811

[56] References Cited

U.S. PATENT DOCUMENTS

| | | | |
|---|---|---|---|
| 3,717,634 | 2/1973 | Wu et al. | 514/252 |
| 3,976,776 | 8/1976 | Wu et al. | 514/252 |
| 4,182,763 | 1/1980 | Casten et al. | 514/252 |
| 4,438,119 | 3/1984 | Allen et al. | 514/252 |
| 4,634,703 | 1/1987 | Kurtz et al. | 514/252 |
| 4,640,921 | 2/1987 | Othmer et al. | 514/252 |

OTHER PUBLICATIONS

Wu, et al., *J. Med. Chem.*, 15, 477–479 (1972), (3/12).
Allen, et al., *Arzneim. Forsch.*, 24, No. 6, 917–922 (1974), (3/14).
Sathananthan, et al., *Current Therapeutic Research*, 18/5, 701–705 (1975) (3/16).
Mattila, et al., *J. Clin. Psychiatry* 43:12(Sec.2), pp. 56–61 (1982) (4/35).
Seppala, et al., *Clin. Pharmacol. Ther.*, 32:2, pp. 201–207 (1982) (4/37).
Cole, et al., *J. Clin. Psychiatry*, 43:12 (Sec.2); pp. 69–74 (1982) (5/2).
Griffeth, et al., *Am. J. Med.*, 80/3B, pp. 30–35 (1986) (5/3).
Meyer, *J. of Studies on Alcohol*, 47/4, 269–273 (1986) (5/5).
Anon, *AMA Drug Evaluations:* 4th Edn., Chp. A pp. 209–214 (1980) American Med. Soc., Chicago, Ill. (5/13).
Blinkerd, et al., *Pharmacologist*, 27/3, 283 (1985) (6/18).
Narangjo, et al., *Clin. Pharmacol. and Therapeutics*, 39/2 215 (1986) (7/3).
Collins, et al., "Buspirone Attenuates Volitional Alcohol Intake in the Chronically Drinking Monkey", *Alcohol*, 4, pp. 49–56 (1987).

*Primary Examiner*—Stanley J. Friedman
*Attorney, Agent, or Firm*—Richard P. Ryan

[57] ABSTRACT

Buspirone and its pharmaceutically acceptable salts are useful in the treatment of alcohol abuse.

15 Claims, No Drawings

METHOD FOR TREATMENT OF ALCOHOL ABUSE

FIELD OF THE INVENTION

This invention is concerned with a drug bioaffecting body-treating process which employs the pyrimidine compound 8-[4-[4-(2-pyrimidinyl)-1-piperazinyl]butyl]-8-azaspiro [4.5]decane-7,9-dione or a pharmaceutically acceptable acid addition salt thereof.

BACKGROUND OF THE INVENTION

The pyrimidine compound with which the present invention is concerned has the following structural formula

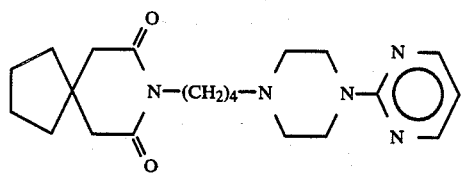

and is known as buspirone. The hydrochloride salt has been referred to in the prior art as MJ 9022-1 and as buspirone hydrochloride. Other acid addition salts thereof are named by combining "buspirone" with the appropriate word to define the acid from which it is prepared as in "buspirone hydrochloride". The latter is the United States Adopted Name (USAN); refer to J. American Med. Assoc. 225. 520 (1973).

The synthesis of the compound and the disclosure of its psychotropic properties are described in the following patents and publications.

1. Y. H. Wu, et al., J. Med. Chem., 15.477 (1972).
2. Y. H. Wu, et al., U.S. Pat. No. 3,717,634 which issued Feb. 20, 1973.
3. L. E. Allen et al., Arzneium. Forsch., 24, No. 6, 917-922 (1974).
4. G. L. Sathananthan, et al., Current Therapeutic Research. 18/5. 701-705 (1975).
5. Y. H. Wu, et al., U.S. Pat. No. 3,976,776, issued Aug. 24. 1976.

The following patent references disclose and claim additional uses which relate to buspirone's pharmacological effects on the central nervous system.

6. The use of buspirone hydrochloride as a novel antianxiety agent for the treatment of neurotic patients is described in G. P. Casten, et al., U.S. Pat. No. 4,182,763, issued Jan. 9, 1980.
7. Allen, et al., disclose the use of buspirone in treating extrapyramidal motor disorders in U.S. Pat. No. 4,438,119, issued Mar. 20, 1984.
8. Buspirone's use in sexual dysfunction was described by Othmer, et al., in U.S. Pat. No. 4,640,921, issued Feb. 3, 1987.
9. Kurtz, et al., in U.S. Pat. No. 4,634,703, issued Jan. 6, 1987 disclose buspirone's use in treating panic disorders.

None of the above-referenced uses would in any way suggest the use of the present invention, a method for controlling and alleviating alcohol (ethanol) abuse.

While the structurally dissimilar benzodiazepine anxiolytics were known to potentiate the effects of alcohol and to successfully serve as a substitute for alcohol in certain patients; buspirone, in contrast, does not interact with alcohol (cf: Mattila, et al., *J. Clin. Psychiatry*, 43:12 (Sec. 2), pp. 56-61 (1982) and Seppala, et al., *Clin. Phar-macol. Ther.*, 32:2, pp 201-207 (1982). In addition, buspirone does not elicit the euphoric mood typical of other known anxiolytic drugs in clinical use such as the benzodiazepines. Besides lacking physical dependence, buspirone also has no clinically demonstrable abuse potential. (cf: Cole, et al., *J. Clin. Psychiatry* 43:12 (Sec 2): pp 69-74 (1982): Griffith, et al., *Am. J. Med.* 80/3B: pp 30-35 (1986). In essence buspirone would not be merely a substitute for alcohol. Meyer in *Journal of Studies on Alcohol*, 47/4, 269-273 (1986) suggests that buspirone be studied for treating persistent anxiety in the postwithdrawal management of alcoholics on the basis that buspirone has a low potential for abuse and does not potentiate the effects of alcohol.

It is appreciated by one skilled in the art that prior art treatments designed to control alcohol abuse employ either "aversion therapy", e.g. disulfiram treatment (cf:*AMA Drug Evaulations:* 4th Edn. Chap. 14 "Drugs Used in Nonpsychotic Mental Disorders" pp. 209-214 (1980) Amer. Med. Soc., Chicago, Ill.) or "substitution", e.g. use of benzodiazepine anxiolytics. Clinical outcome of these treatments are controversial and do not represent effective treatment for the majority of patients that are chronic alcohol abusers.

Disulfiram (Antabuse ®) is the only approved drug treatment for chronic alcohol abuse in the U.S. today. It causes a highly unpleasant reaction to alcohol ingestion but provides no other benefit to the chronic abuser of alcohol. Benzodiazepine anxiolytics are used in acute alcohol withdrawal treatment. However, these agents are not useful for definitive treatment of alcohol abuse since they substitute quite nicely for alcohol and can lead to a new dependence. It should be understood that no drug which actually treats the disorder of alcohol abuse per se is available. There is in fact, no really satisfactory drug treatment for abuse of alcohol at the present time.

It should also be appreciated that abuse of alcohol is a disorder affecting a large number of people and exacts a high cost in both physical and mental anguish. It has been estimated by The National Institute on Alcohol Abuse and Alcoholism that there are as many as 10 million alcoholics and problem drinkers in the U.S. alone. World estimates are several times as many.

There have been reports of agents that reduce alcohol intake in both animal and human studies.

The drug fluoxetine has been reported to reduce alcohol intake in rats, cf: Blinkerd, et al., *Pharmacologist*, 27/3, 283 (1985).

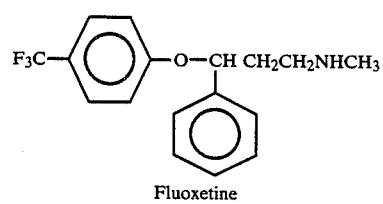

Fluoxetine

The drug zimelidine has been reported to reduce ethanol intake in rats and in non-depressed alcohol abusers. cf: Narangjo, et al., *Clin. Pharmacol. and Therapeutic*, 39/2, 215 (1986).

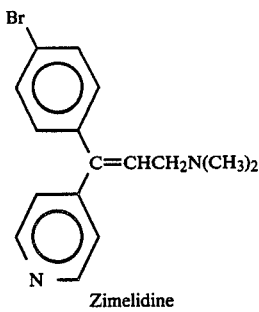

Zimelidine

As can be seen, there is no structural similarity between buspirone and fluoxetine, zimelidine, and the benzodiazepine class of compounds.

In summary, there exists nothing in the prior art, including the specific references set forth hereinabove, which would make obvious the use of buspirone to treat the abuse of alcohol.

SUMMARY OF THE INVENTION

The method of the present invention is intended for the treatment of alcohol abuse in patients that exhibit that disorder. The method essentially involves administration of buspirone, or a pharmacologically acceptable acid addition salt thereof, to a patient in need of such treatment. For use in the instant method oral administration of buspirone hydrochloride from about 10 to 80 mg per day in divided doses is anticipated as being the preferred dosage regimen.

DETAILED DESCRIPTION OF THE INVENTION

Abuse of alcohol (ethanol) is a disorder characterized by continued excessive or compulsive ingestion of alcoholic beverages and this behavior is believed by many to overlay a complex chronic psychological and nutritional disorder. There is at present no treatment which is accepted as being broadly effective for this group of patients. Treatments that are used may be classified as either psychotherapy or psychopharmacology. Counseling, participation in self-help groups such as Alcoholics Anonymous, and the like comprise psychotherapy. Use of pharmacologic agents to treat alcohol abuse mainly involves administration of an adversive agent to ethanol such as disulfiram which causes nausea, flushing, and so forth when alcohol is ingested or the administration of an alcohol substitute such as the euphoria-producing benzodiazepines in the acute treatment of the alcohol withdrawal syndrome. A further problem with the benzodiazepines is that they interact with alcohol to potentiate its effects, thereby exacerbating the patient's condition if alcohol is ingested concomitantly. This would result initially in a much greater impairment of the alcohol abuser's faculties and enhancement of intoxication side-effects with accompanying risks.

An objective of the present invention is to provide a broadly effective method for treating alcohol abuse which avoids enhancement or continuation of sensory impairment, risk of developing drug dependence, and the highly unpleasant effects of "aversion" therapy.

Buspirone has now been found to be effective in treating alcohol abuse. Treatment of alcohol abuse with buspirone encompasses the active drinking, the acute withdrawal, and long-term maintenance periods of the alcohol abuser. Administration of buspirone results in desireable behavioral modification and in alleviation of psychogenic symptomatology associated with alcohol abuse. Modification of behavior involves reducing the craving for alcohol and improvement in social functioning. Most commonly associated psychogenic symptoms of alcohol abuse comprise anxiety, depression, decreased cognition, clouded sensorium, hostility and violence.

Clinical study of buspirone administration for the treatment of alcohol abuse has demonstrated its effectiveness and safety in an in-patient population undergoing acute withdrawal. One notable effect in these patients was a "rapid clearing the sensorium" which was induced by buspirone. This effect has not been reported for any other drug. It is felt that clouded sensorium and decreased cognition contribute to a relapse toward alcohol abuse in patients. Similarly the anxiety and depression associated with alcohol abuse also seem to be related with relapse. These considerations suggest that long-term treatment may be necessary to control alcohol abuse. The lack of physical dependence and abuse potential for buspirone make it even more attractive for long-term use in chronic cases of alcohol abuse. The effectiveness of buspirone in alleviation of symptoms associated with alcohol abuse as well as modification of behavior concerning alcohol preference and consumption has been demonstrated clinically.

In a double-blind, parallel group, placebo-controlled study, 50 chronic alcoholics were divided into 2 groups of 25 patients each and administered either buspirone or placebo medication. These study patients met DSM-III (American Psychiatric Association: Diagnostic and Statistical Manual of Mental Disorders. Third Edition. Washington. D. C. APA, 1980) criteria for alcohol abuse of at least 2 years duration. Each patient group was to receive 8 weeks of medication—either buspirone or placebo and was to be evaluated during the study for alcohol related behavior and symptomatology which comprised the study for alcohol craving, drinking behavior, social interactions, anxiety, depression, short-term memory, and global psychopathology. These items were evaluated by means of standard psychometric rating instruments and scales. The buspirone treatment group exhibited statistically significant improvement compared to placebo treatment in social interactions, global ratings and in decreasing alcohol craving, drinking behavior, anxiety and depression.

The present invention then may be described in summary as follows. Buspirone, a drug structurally unrelated to any presently used agent in treatment of alcohol abuse, has been demonstrated to be effective not only in patients undergoing short-term treatment for alcohol withdrawal but also in an 8-week controlled clinical study of patients that were chronic alcohol abusers. The method of the present invention essentially involves administration of buspirone, or a pharmaceutically acceptable salt thereof, to a patient in need of such treatment. Buspirone treatment would be indicated both for alleviation of alcohol abuse symptomatology: illness, anxiety, depression, clouded sensorium, hostility and violence, reduced cognition and the like; as well as acting to improve the patient social interactions and drinking behavior comprising craving for and ingestion of alcohol.

Pharmaceutically acceptable acid addition salts of buspirone and methods of pharmaceutical formulation are described in the patents of Wu, et al., U.S. Pat. Nos.

3,717,634 and 3,976,776 which are incorporated in their entirety herein be reference.

Administration of buspirone according to the present invention may be made by the parenteral, oral or rectal routes. Parenteral administration comprises injection, e.g. intravenous or intramuscular injection; as well as any other parenteral route of administration. The oral route is preferred, however, the clinical dosage range for alleviation of alcohol abuse is expected to be about the same to slightly higher compared with that for anti-anxiety usage, but can vary to some extent. In general, the expected amount of buspirone administered would be less than about 100 mg per day, generally in the 20 mg to 80 mg range, and preferably in the range of 30–60 mg per day. Since the dosage should be tailored to the individual patient, the usual practice is to commence with a dose of about 5 mg administered two or three times per day and then to increase the dose every two or three days by 5 mg at each dosage time until the desired response is observed or until the patient exhibits side effects. Single daily dosage may be applicable in some instances.

What is claimed is:

1. A method for treatment of alcohol abuse, comprising modification of alcohol abuse behavior and alleviation of psychogenic symptomatology associated with alcohol abuse, which method comprises administering a non-toxic alcohol abuse modifying dose of buspirone or a pharmaceutically acceptable acid addition salt thereof to a patient in need of such treatment.

2. The method of claim 1 wherein the method is employed for modification of alcohol abuse behavior, such modified behavior comprising lessened craving for alcohol, lessened ingestion of alcohol, and improved social functioning.

3. The method of claim 1 wherein the method is employed for alleviation of psychogenic symptomatology associated with alcohol abuse, such symptomatology comprising illness, anxiety, depression, clouded sensorium, hostility and violence, and decreased cognition.

4. The method of claim 1 wherein buspirone hydrochloride is employed and dosage is by the oral route.

5. The method of claim 4 wherein a daily dose of about 10 to 80 mg is employed.

6. The method of claim 5 wherein said daily dose is divided and administered b.i.d.

7. The method of claim 5 wherein said daily dose is divided and administered t.i.d.

8. The method of claim 2 wherein the modified behavior is a lessened craving for alcohol.

9. The method of claim 2 wherein the modified behavior is a lessened ingestion of alcohol.

10. The method of claim 2 wherein the modified behavior is improved social functioning.

11. The method of claim 2 wherein the symptomatology is illness.

12. The method of claim 2 wherein the symptomatology is depression.

13. The method of claim 2 wherein the symptomatology is a clouded sensorium.

14. The method of claim 2 wherein the symptomatology is hostility and violence.

15. The method of claim 2 wherein the symptomatology is a decreased cognition.

* * * * *